United States Patent
Merck, Jr. et al.

(10) Patent No.: US 6,247,356 B1
(45) Date of Patent: *Jun. 19, 2001

(54) HARDNESS TESTER

(75) Inventors: John J. Merck, Jr., Medfield; Richard Conti, Foxboro; Joerg Meissner, Medfield; Patrick Micozzi, Acton, all of MA (US)

(73) Assignee: Instron Corporation, Canton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/281,449

(22) Filed: Mar. 30, 1999

(51) Int. Cl.$^7$ ........................................ G01N 3/42
(52) U.S. Cl. ........................................... 73/82
(58) Field of Search ............................ 73/81, 82, 83, 73/85

(56) References Cited

U.S. PATENT DOCUMENTS

| | | |
|---|---|---|
| 4,435,976 | 3/1984 | Edward, Jr. . |
| 4,535,623 * | 8/1985 | Giberto ........................ 73/81 |
| 4,807,465 * | 2/1989 | Botzolakis et al. ................ 73/78 |
| 5,140,861 * | 8/1992 | Gleason et al. .................. 73/865.8 |
| 5,164,998 * | 11/1992 | Reinsch ......................... 382/65 |
| 5,177,999 | 1/1993 | Tobolski . |
| 5,181,416 * | 1/1993 | Evans ........................... 73/81 |
| 5,297,440 * | 3/1994 | Rizk et al. ...................... 73/849 |
| 5,305,633 * | 4/1994 | weissenbacher et al. ............ 73/82 |
| 5,486,924 * | 1/1996 | Lacey ........................... 73/81 |
| 5,616,857 | 4/1997 | Merck et al . |
| 5,866,801 * | 2/1999 | Johnson et al. ................... 73/38 |

* cited by examiner

Primary Examiner—Hezron Williams
Assistant Examiner—Katina M Wilson
(74) Attorney, Agent, or Firm—Levisohn, Lerner, Berger and Langsam (57) ABSTRACT

A hardness tester having a frame and a rotatable turret movably supported on the frame is provided. A plurality of load cells are fixedly mountable on the turret, and a plurality of indenters are fixedly attachable to the load cells, respectively. A user interface selectively provides signals to a motor to move the turret into contact with a test specimen via one of the indenters to thereby apply a load on the test specimen. The indenters are fixed with respect to the turret and do not move in relation to the turret when the turret is brought down to bear on the test specimen. The load cells measure the load applied to the test specimen. A closed loop control system receives load measurement signals from the load cells and controls movement of the turret, preventing the motor from applying load in excess of a predetermined selectable load amount input by a user via the user interface. The invention preferably includes a plurality of indenter adapters, each attached to respective undersides of the load cells. Each indenter adapter includes a slot into which the indenter is fittable, and least one set screw for adjusting a horizontal location of the indenter.

23 Claims, 7 Drawing Sheets

HARDNESS TESTER

BACKGROUND OF THE INVENTION

1. Field of the Invention

The invention relates to hardness testers, and more specifically to penetration hardness testers that can perform more than one type of penetration hardness test.

2. Description of Related Art

Penetration hardness testers are well-known in the art, and generally include a diamond or ball tipped penetrator and means to apply minor or major loads of predetermined magnitudes through the penetrator to a test specimen in successive load cycles. The hardness of the surface being tested produces results such as a Rockwell number or Brinell number. The hardness is related to the depth of penetration of the penetrator into the surface when a selectable value of compressive force is applied to the penetrator. Optical measurement of diagonal length of an indentation is performed for Vickers and Knoop tests, for example.

In prior art Rockwell type hardness testers, the force that is exerted on the penetrator is produced by gravity acting on weights, and this in turn is transferred by mechanical means to the penetrator. The depth of penetration is generally directly measured from the tool and generally displayed on a dial indicator, digital display or other display apparatus. Prior art apparatus requires gravity acting on weights, and the measurement of the tool movement through mechanical assemblies is subject to impreciseness as the tester is repeatedly utilized subjecting the apparatus to wear through repeated mechanical movement.

The use of deadweight testers and their mechanical impreciseness over time has led to the use of a load cell as part of the means to measure the application of force to the test specimen. An example of a system employing a load cell is found in U.S. Pat. No. 4,535,623 entitled Material Hardness Testing Apparatus by Paul Gilberto, a patent assigned to a predecessor of the assignee of the present application and now owned by the instant assignee. In the '623 patent, a load cell is located adjacent the penetrator, and deadweights are avoided in conducting the hardness tests. A mechanical threaded advancing means is employed to apply the load to the test specimen, and the load on the load cell is related to the force on the test specimen. The mechanical action in the '623 patent for applying force by the tester, by its very nature, will, over time cause impreciseness because of the relative movement of the threaded screw and its driven elements. Such inaccuracies can become significant in the measurement process as the underlying measurements are used as a basis for many determinations thereafter.

The use of feedback control closed loop systems can lessen the impreciseness which is attendant to materials hardness tests. U.S. Pat. No. 4,435,976 describes the use of a load cell to determine the forces applied during Brinell tests and employs a feedback loop to automatically compensate factors which affect the accuracy of the measurements, such factors being temperature and friction. The apparatus in the '976 patent utilizes a mechanical bearing connected between the indenter and the load cell, which mechanical bearing, itself, can cause inaccuracies in the measurement process because of its repeated mechanical movement and the wearing of the bearing.

The indenter will penetrate to some depth or displacement in the test specimen. A measurement is made of the displacement, and in prior art penetration hardness testers, there are moving mechanical parts which move relative to each other located between the actual displacement and measured displacement. Such relative mechanical movement can contribute to sources of friction or lost (non-recoverable) displacement between the point of displacement measurement and the test specimens so as to impair the repeated accuracy of the hardness test.

All known bottom-referencing type hardness testing machines, both using load cell or deadweight style, employ an elevating screw to accommodate different specimen sizes. The mechanical forces employed in the elevating screw also can contribute to degradation of displacement measurement accuracy because of the possibility of additional deflection loss which can contribute to the inaccuracy of the displacement measurement. U.S. Pat. No. 5,616,857 to Merck et al. and assigned to the instant assignee (the teachings of which are incorporated herein by reference), for example, teaches the use of different sized platforms for mounting and supporting specimens in lieu of an elevating screw.

The use of load cells has increased the accuracy of hardness testers. However, load cells are made less accurate by increasing the amount of dead weight hanging therefrom. Weight and/or structure below the load cell creates dynamic forces that decrease the accuracy of the load cell readings.

Another drawback to conventional microhardness testers is that they cannot be easily reconfigured from being able to perform one type of hardness test to being able to perform another. This detraction can be particularly inconvenient when it is desired to perform more than one test on the same specimen. An interesting non-microhardness tester is taught in U.S. Pat. No. 5,177,999 to Tobolski et al., assigned to a predecessor in interest to the instant assignee and now owned by the instant assignee (the teachings of which are incorporated herein by reference). Tobolski et al. teach the provision of several indenters mounted on a rotatable turret. The turret is brought down to the specimen, and the spring-loaded indenter provides an indentation. If a second test is desired, the turret is rotated so that a different indenter is positioned over the specimen. A dead weight assembly provides the load in the Tobolski patent. Because the indenters are spring loaded, they move with respect to the turret. As a result, additional moving parts render the load applications and measurements thereof less accurate, in that there are greater opportunities for dead mechanical movement in the system. Moreover, one is limited in the number of different indenters one may use by the availability of mounting spots on the turret.

SUMMARY OF THE INVENTION

Accordingly, it is an object of this invention to provide an improved hardness tester which eliminates the inaccuracies of prior hardness testing apparatus.

Another object of the present invention is to provide such an improved apparatus which is easy to operate, substantially unchanging over time and location and produces reliable and accurate results.

Another object of this invention is to provide such an apparatus which advantageously employs current technology to provide improved results and may be readily adapted to provide additional test data.

Another object of the invention is to provide a penetration hardness tester that is capable of performing more than one type of hardness test.

Another object of the invention is to provide a penetration hardness tester that is capable of easily switching between being able to perform more than one type of test.

Another object of the invention is to provide a penetration hardness tester upon which it is easy to mount and replace different indenters.

Another object of the invention is to provide a penetration hardness tester which operates over a large ranges of forces.

Other objects, advantages, and features of this invention will become apparent from the description of the invention which is a hardness tester having a first frame and a rotatable turret movably supported on the first frame. A motor is movably supported on the first frame; the motor is connected to the turret and selectively moves the turret with respect to the first frame. A plurality of load cells are fixedly mountable on the turret, and a plurality of indenters are fixedly attachable to the load cells, respectively. A user interface is provided electrically connected to the load cells and the motor. The interface selectively provides signals to the motor to move the turret into contact with a test specimen via one of the indenters to thereby apply a load on the test specimen via the one of the indenters. The indenters are fixed with respect to the turret and do not move in relation to the turret when the turret is brought down to bear on the test specimen. The load cells measure the load applied to the test specimen.

In a preferred embodiment, the invention further includes a second frame, movably mounted on the first frame. The turret is rotatably mounted to the second frame. The motor is connected to the second frame, and the motor selectively moves the second frame with respect to the first frame. The invention preferably further includes a closed loop control system electrically connected to the motor and the load cells and the user interface. The closed loop control system receives load measurement signals from the load cells and controls movement of the second frame, preventing the motor from applying load in excess of a predetermined selectable load amount input by a user via the user interface. Preferably, the invention includes a plurality of indenter adapters, each attached to respective undersides of the load cells. Each indenter adapter includes a slot into which the indenter is fittable and at least one set screw for adjusting a horizontal location of the indenter.

The only weight below the load cell in the instant invention is the indenter and the indenter adapter. The removal of weight and/or structure below the load cell decreases the amount of dynamic forces that could be created and thus decreases the inaccuracy of the load cell readings. Also, by providing indenters that are fixed with respect to the turret, the invention has fewer moving parts and is more accurate, in that there are fewer opportunities for dead mechanical movement in the system. Finally, the inventive indenter adapters allow for different indenters to be mounted and removed from the turret quickly and easily. The indenter adapters also enable the user to make fine adjustments on the position of the indenter.

DETAILED DESCRIPTION OF THE PREFERRED EMBODIMENTS

Figure 1:
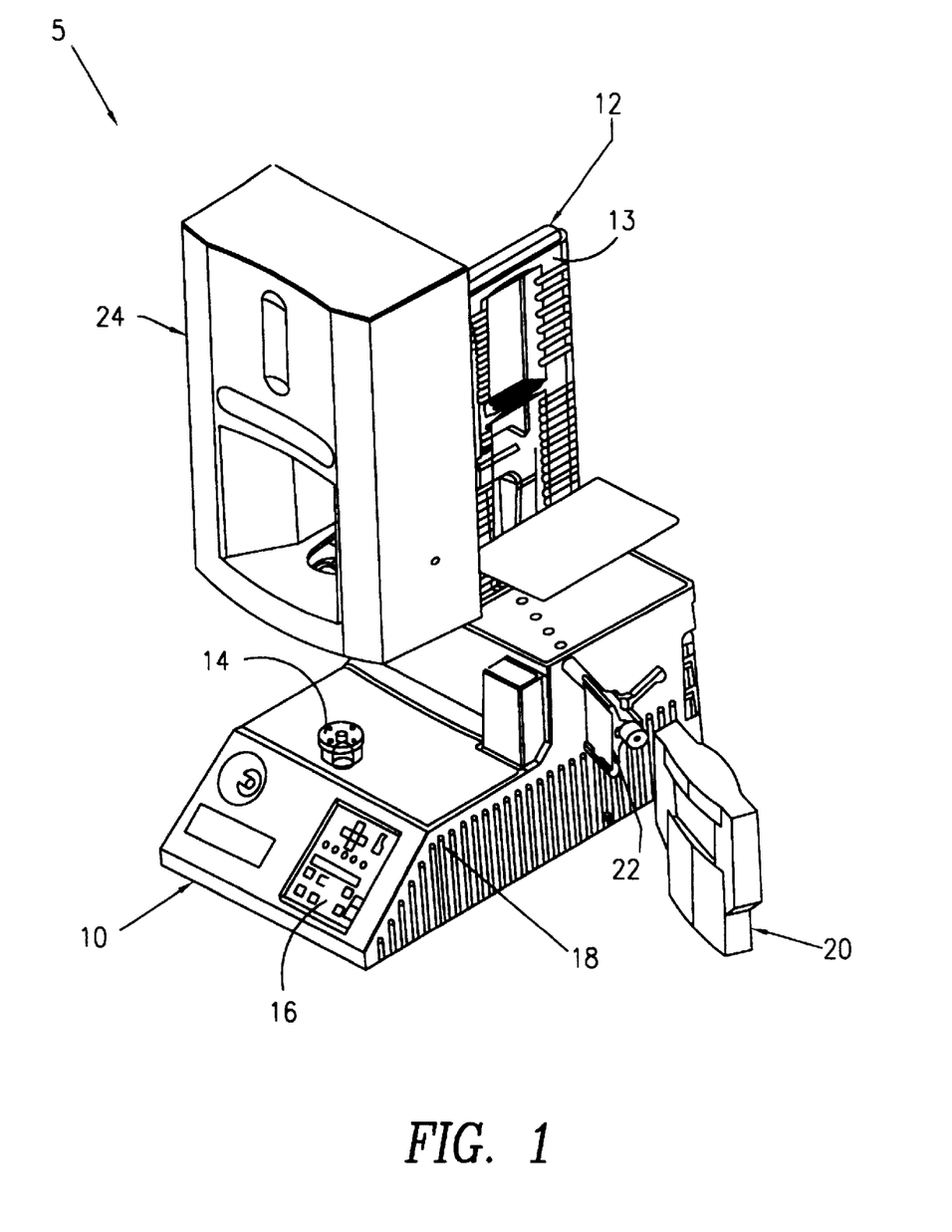
FIG. 1 is a perspective view of the exterior of a preferred hardness tester according to the invention.
Figure 2A:
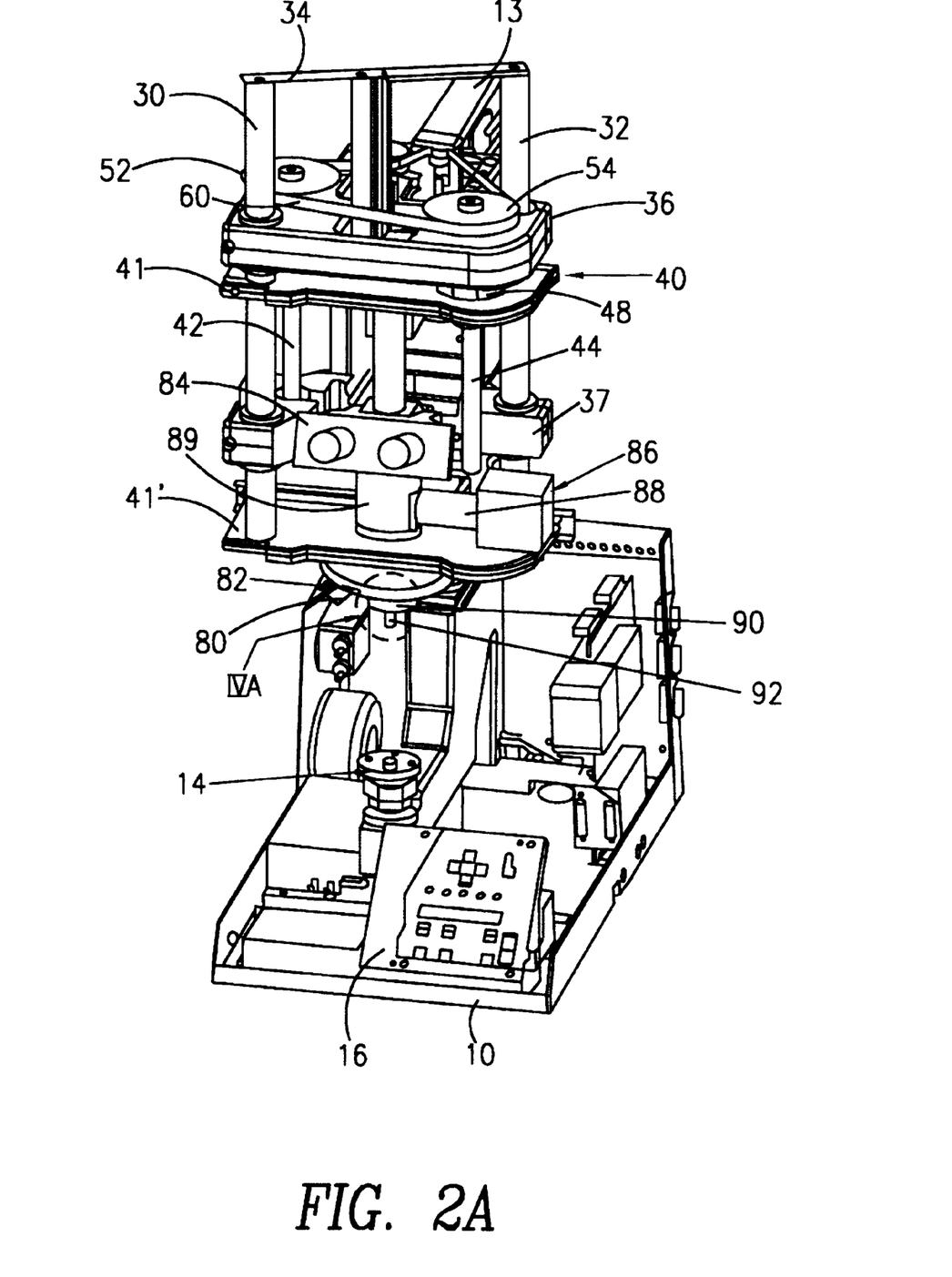
FIG. 2A is a front perspective view of the hardness tester of FIG. 1 with the cover removed.
Figure 2B:
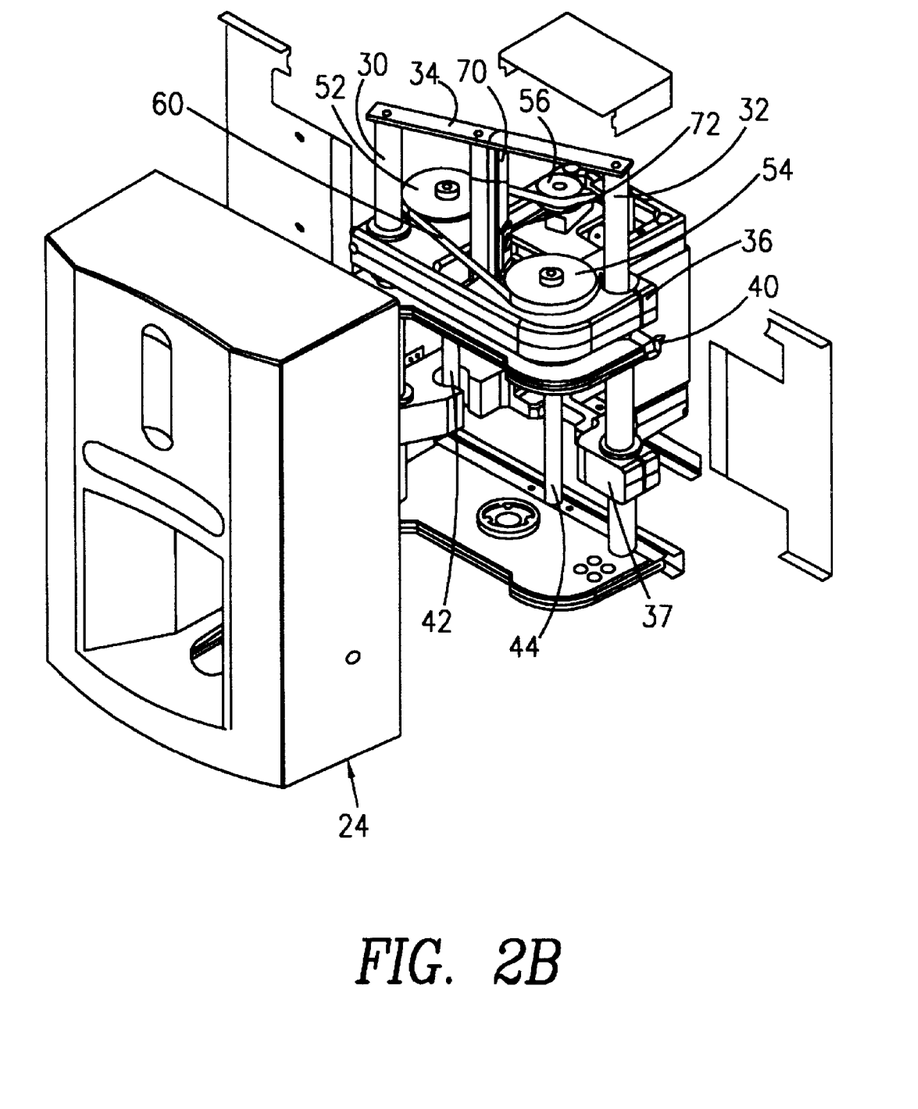
FIG. 2B is side exploded perspective view of the some of the internal components of the hardness tester of FIG. 2B.

Description will now given of the inventive hardness tester with reference to FIGS. 1–5. As shown in FIGS. 1–2B, the inventive tester 5 includes a base and a support frame 12. Support frame 12 is fixed to the base and serves as the structural foundation of tester 5. In FIG. 1, only rear support 13 is visible. Mounted on base 10 is a specimen stand 14. Specimens are placed on stand 14 for hardness testing purposes. A control panel 16 and interactive display 20 enables the user to select and modify the various parameters of the testing process, including the amount of load to be delivered to the specimen, which indenter is to be used, focusing of objectives, and the like . The user can see the results of the test on user interface display 20. A bracket 22 can be used to mount display 20; the bracket allows the display 20 to be tilted for sitting or standing user modes of operation. The lower interior elements of tester 5 are shielded from dust and otherwise protected by cover 18, and the upper moving interior elements of tester 5 are protected by main cover 24.

As shown in FIGS. 2A–B, support frame 12 includes support columns 30 and 32 which are connected by a brace 34. The support frame also includes an upper support platform 36 and a lower support platform 37. Moveably mounted on the support frame is a movable turret frame 40. Frame 40 includes upper cross-support 41 and lower cross-support 41'. Upper and lower cross-supports 41 and 41' include bores through which support columns 30 and 32 pass. Upper cross-support 41 also accommodates long screws 42 and 44 which provide the means for moving the turret frame 40 with respect to support frame 12. Each of long screws 42 and 44 has a nut attached to it between upper cross-support 41 and upper support platform 36.

Figure 3A:
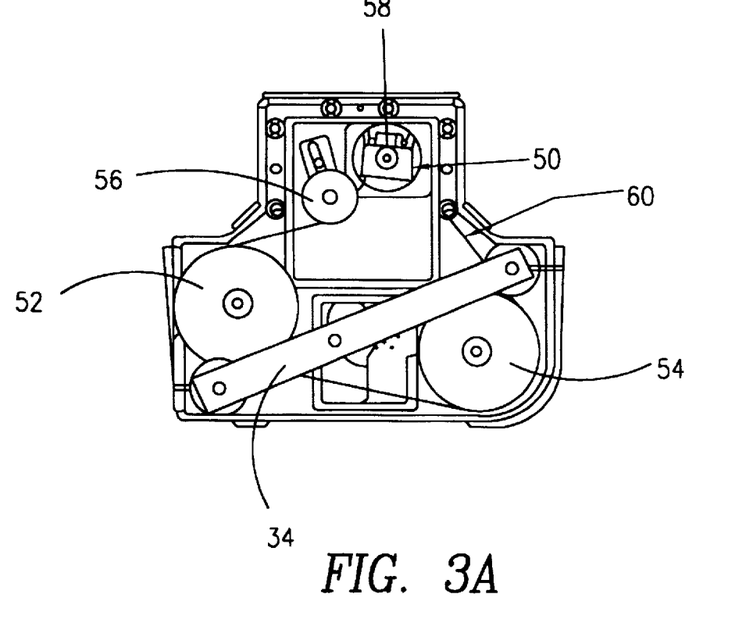
FIG. 3A is a top plan view of the frame and motive components of a hardness tester according to the invention.
Figure 3B:
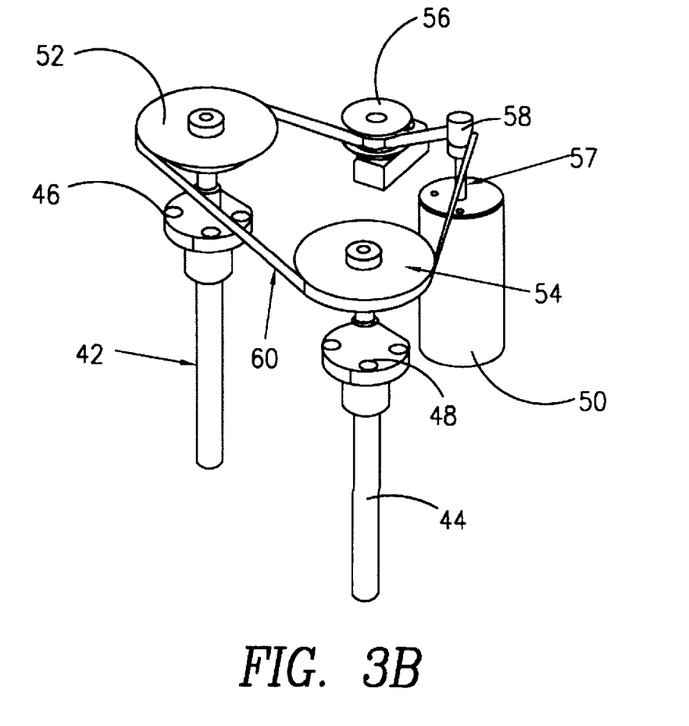
FIG. 3B is an exploded perspective view of the motive components depicted in FIG. 3A.

The motive power for moving turret frame 40 vertically with respect to support frame 12 is supplied by motor 50 (see FIGS. 3A–B). Several pulleys 52, 54, and 56 are employed to transfer torque from motor 50. Motor 50 is provided with shaft 57 and shaft extender 58. A drive belt 60 is connected to all of pulleys 52, 54, and 56 as well as shaft extender 58. Pulleys 52 and 54 are attached to long screws 42 and 44, respectively. Idle pulley 56 is provided to take up slack on drive belt 60. When motor 50 is activated, shaft 57 rotates, causing drive belt 60 to rotate pulleys 52, 54, and 56. The rotation of pulleys 52 and 54 causes long screws 42 and 44 to rotate. Because nuts 46 and 48 are fixedly mounted to turret frame 40 and threaded around screws 42 and 44, the rotation of screws 42 and 44 causes turret frame 40 to move along the screws, either up or down depending on the direction of the rotation of the screws. In this way, the motor 50 can move turret frame 40, and thus turret 80, closer to or further from a test specimen mounted on stand 14. As shown in FIG. 2B, a scale 70 is provided fixed to the support frame 12, and an optical sensor 72 is fixed to turret frame 40. The position of the turret frame 40, and thus the indenters on the turret, can be determined by sensor 72 and used as explained below.

The support columns 30 and 32, screws 42 and 44, platforms 36 and 37, frame 40, motor 50, and the associated pulleys and nuts are collectively called the actuator. In one embodiment, the actuator is mounted on rear support 13 but is modularly removable; that is, the entire actuator assembly may be removed and mounted in a different system.

Attached to the bottom portion of lower cross-support 41' is turret 80, upon which are mounted one or more optical objectives 82. An optical assembly 84 is provided in line with the working position of turret 80, i.e., the position of the turret that is directly above a test specimen placed on stand 14. A user of the microhardness tester may look into optical assembly 84 to view a sample on stand 14 in a magnified fashion so as to examine indentations made by the indenters of the hardness tester. Microscope illuminator 86 is connected to optical housing 89 via connector 88. Illuminator 86 provides a light source to aid the user in examining the specimen.

Figure 4A:
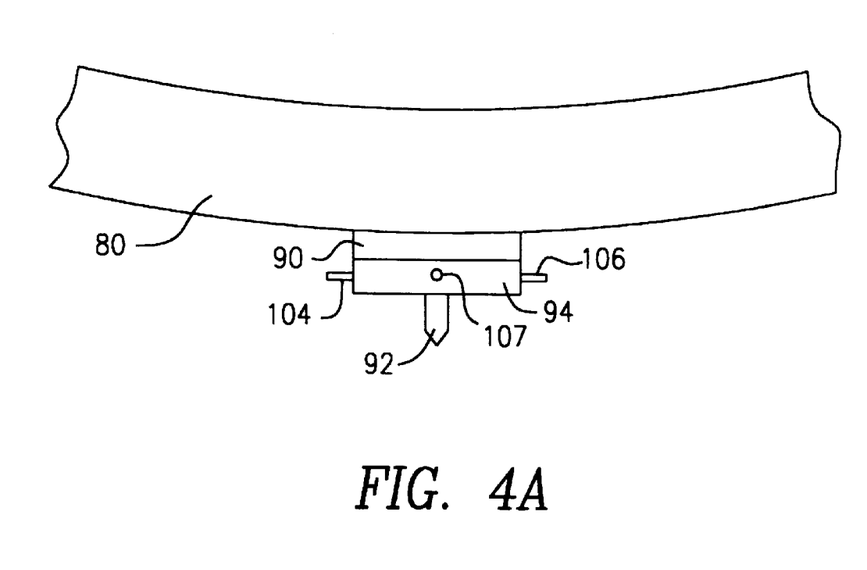
FIG. 4A is an enlarged front plan view of the turret, load cell, and indenter adapter according to the invention.
Figure 4B:
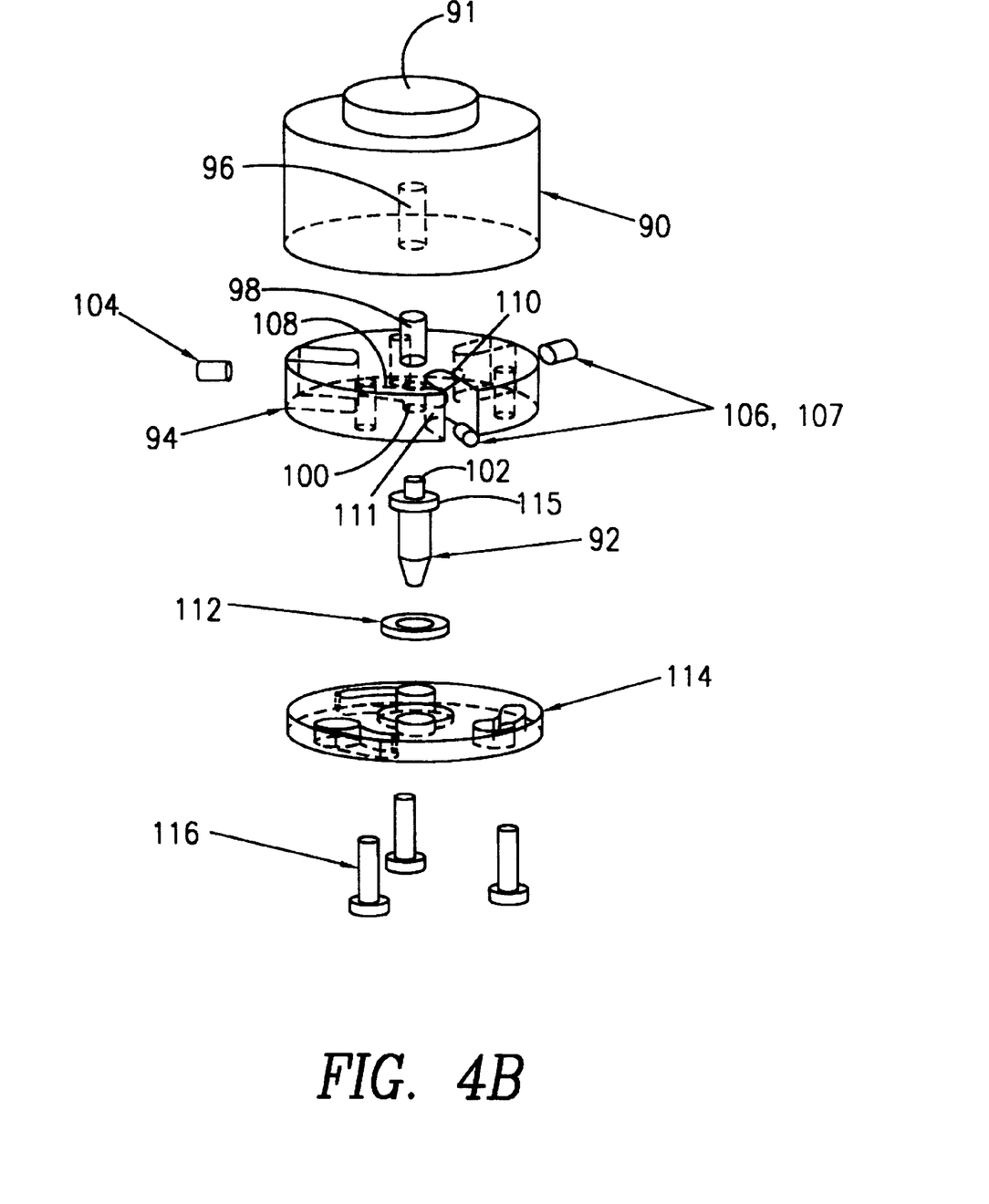
FIG. 4B is an exploded partially transparent perspective view of the load cell and indenter adapter according to the invention.
Figure 5:
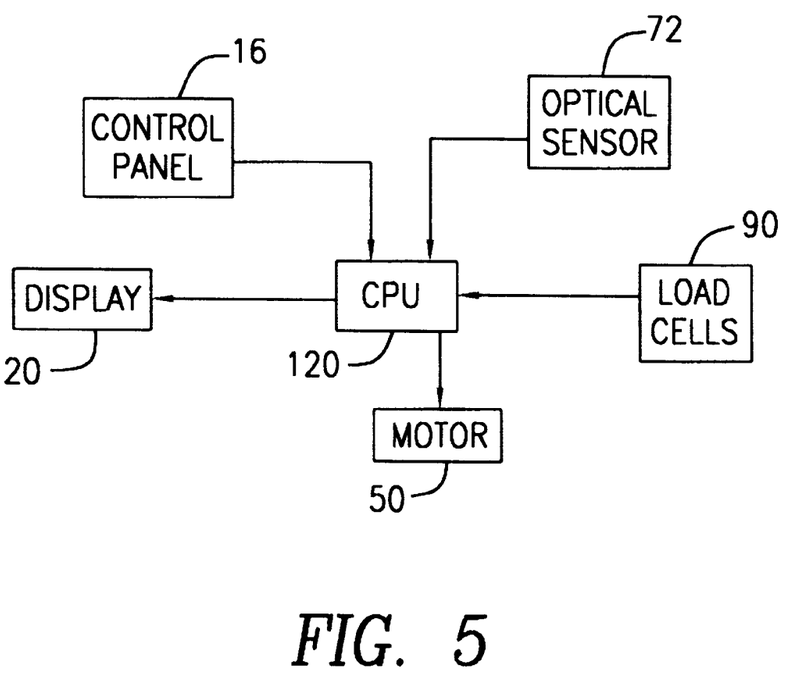
FIG. 5 is a schematic of the closed loop feedback control system of the present invention.

Also attached to the turret 80 are load cells 90 and indenters 92 mounted thereon (see FIGS. 2A and 4). A plurality of indenters 92 is preferably provided so that a plurality of indentation tests (e.g., Vickers, Knoop, etc.) may be performed by the same tester on the same specimen without removing or replacing an indenter from the turret. When it is desired to perform a first microhardness test (e.g., Vickers), the turret is rotated so that the corresponding indenter 92 is in the working position over the specimen. If a different microhardness test (e.g., Knoop) is subsequently to be performed on the specimen, the turret is again rotated so the second indenter 92 corresponding to the second test is in the working position over the specimen. In one embodiment of the invention, the user manually rotates the turret 80 to position the desired objective 82 or indenter 92 in the working position above the specimen. In another embodiment, the turret 80 is provided with a rotator (not shown) which is controllable via the control panel 16; the user selects the desired objective or indenter via entering the proper keystrokes on the control panel.

The precise horizontal positioning of the indenter 92 with respect to the specimen is enabled by the inventive indenter adapter shown in FIG. 4. Load cell 90 is attached to turret 80 via attachment piece 91. Attachment piece 91 may be threaded so that the load cell 90 screws into a threaded recess in the turret 80. Alternatively, attachment piece 91 may be magnetic, spring loaded, or the like. Beneath load cell 90 is attached an indenter adapter 94. Load cell 90 includes a slot 96 for receiving a mounting pin 98 protruding upwards from indenter adapter 94. Indenter adapter 94 is provided with a slot 100 for receiving mounting pin 102 of indenter 92. Pin 102 is not threadedly attached to slot 100. Rather, three screws 104, 106, and 107 are fitted into bores 108, 110, and 111 respectively, and they secure pin 102 inside slot 100. Pin 102 is machined about ½ mm smaller in diameter than slot 100. Screw 104 is spring loaded and exerts force against pin 102 to keep it snugly within slot 100 and abutting against set screws 106 and 107. Screws 106 and 107 are not spring biased but can be turned to adjust the position of pin 102 within slot 100. Bores 108, 100, and 111 are provided in indenter adapter 94 through which the set screws 106 and 107 and the spring screw 104 pass to contact pin 102 in slot 100. A spring wave washer 112 and adapter clamp 114 are provided to maintain indenter 92 abutted against indenter adapter 94. Screws 116 secure clamp 114 to adapter 94. Screws 116 are made tight enough so that spring wave washer 112 can exert a retaining force against the flange 115 of indenter 92, but are loose enough so that the horizontal position of indenter 92 may be adjusted by the rotation of set screws 106 and 107.

The inventive hardness tester includes a closed loop feedback control system for enabling the proper amount of load to be supplied to the specimen. A central processing unit 120 (CPU) is provided, as shown schematically in FIG. 5, in the feedback loop. The closed loop system is responsive to loads applied to the indenter 92 and the test specimen by setting a desired load in the CPU 120 via control panel 16 and sensing the load applied at the load cell 90.

Another aspect of the present invention is the ability to accurately control the rate of application of the load, and the control system of this invention provides means to determine the rate of application of the load system.

The control loop of the present invention is a proportional integral derivative gain control loop with real time stiffness compensation. This type system enhances sensing an error signal in the closed loop to intensify the sensitivity of the apparatus. The use of the optical sensor 72 and scale 70 provides indenter displacement information. Fiber optic and/or laser devices may also be effectively used to sense the position or location of the turret frame 40 and thus the position of indenter 92.

The invention can also protect the indenter from accidental damage. For example, if the turret is moving is a non-test mode, e.g., when one is moving the turret into position to begin a test, any load sensed by the load cell will halt the movement of the turret, since the turret is not supposed to encounter any resistance in a non-test mode. This is accomplished by CPU 120 operating in the closed loop feedback control system.

Also, the dwell time of the indenter can be varied. A user may program the indenter to apply the desired load for a predetermined period of time. Such a command would be enterable via user interface display 20, for example.

In accordance with an aspect of the present invention, by employing a closed loop system with motor 50, pre-test positioning may be achieved much more quickly. By employing the central processing unit 120, improved data gathering is realized including scale changing and other aspects of the testing procedures. Further, in addition to the rate of application of the load, the amount of penetration as well as other parameters in the measuring process may also be sensed and utilized to further define the mechanical properties of the materials being tested. The tester includes the ability to produce related pairs of information about the displacement and related load. The tester, therefore, can identify and cancel out any displacements not specifically the result of specimen deformation, as well as locate the surface of the specimen from the data pairs. As a result, the tester can determine the actual depth of indenter penetration into the specimen for any given load.

In the present invention, there is less mechanical movement between connected parts that can affect test results, and the elimination of such mechanical movement decreases the number of inaccuracies due to friction, dirt buildup, and repeated mechanical use. This is especially true with the load cell being directly coupled to the indenter without intervening moving parts, and this is further made advantageous by the direct mounting of a fixed non-moving indenter onto the turret. Thus, all moving mechanical parts are within the closed loop system; as a result, friction, dirt buildup, and mechanical wear no longer affect the force applied. This provides more reliable, repeatable testing over time and allows better comparison of data obtained from testers in different locations.

As a feature of this invention, "smart" indenters may be employed with this system in which calibration factors for different measurements can automatically be loaded into the system to automatically compensate for changes or differences which occur in the different indenters.

In operation, the invention is used as follows. A test specimen is placed on stand 14, and it is desired to perform several different microhardness tests on the specimen. A user enters commands into control panels 16 and 20 so as to cause a specific type of test to be performed with a specific load. Other variables, such as indenter dwell time, may be programmed in this manner. The user selects which indenter he wants to use for the test. This can be done either manually or automatically, depending on the embodiment of the invention, as described above. The control panels 16 and 20 forward the commands as electric signals to CPU 120, which in turn controls the actuation of motor 50. Motor 50 is activated and causes turret frame 40 to move downwardly towards the specimen. As turret frame 40 moves, optical sensor 72 senses the position of the turret frame 40 by reading the scale 70 fixed to the support frame 12. When the indenter 92 contacts the test specimen, load cell 90 senses that contact and relays that information to the CPU 120. The CPU makes note of the no-load first contact position of the turret based on the position reading of optical sensor 72. Thereafter, CPU 120 sends signals to motor 50 to continue to provide torque to long screws 42 and 44 and thereby continue to move turret 80 downwards. Because the indenter 92 is contacting the specimen, the continued application of motive power by motor 50 causes the indenter to exert a load on the specimen and thus leave an indentation in the specimen. The load cell 90 senses the load being applied and reports that load measurement back to the CPU. When the load sensed by the load cell 90 is equal to the predetermined load selected by the user, the CPU 120 disengages the motor 50 so that the specimen is not further loaded. The change in position from the point where the indenter 92 first contacted the specimen until the point where the desired amount of load is reached is equal to the depth of the indentation made in the specimen. This depth measurement is displayed on display 20 along with other pertinent information. If the user wishes to examine the actual indentation, the user rotates turret 80 so that optical objective 82 is in the working position above the indentation. The user activates microscopic illuminator 86 and peers into optical assembly 84. Should another test be desired, the user rotates the turret 80 so that the second indenter is aligned over the specimen.

This invention has been described with reference to a preferred embodiment and other embodiments are considered within the scope of this invention as defined by the appended claims. For example, any number of different indenters and objectives may be provided on the turret. Also, although the drawings depict two set screws and one spring-loaded screw being used in the indenter adapter, any convenient number of screws may be employed in the indenter adapter to enable the user to position the indenter precisely in the horizontal plane. Further, the drawings depict a turret that is movable in a vertical direction with respect to the fixed support frame. However, the invention is not so limited; rather, the invention includes a hardness tester in which the movable turret frame moves horizontally with respect to the fixed support frame as well.

What is claimed is:

1. A hardness tester, comprising:
    a first frame;
    a rotatable turret movably supported on said first frame;
    a motor movably supported on said first frame, said motor connected to said turret, said motor selectively moving said turret with respect to said first frame;
    a plurality of load cells fixedly mountable on said turret;
    a plurality of indenters fixedly attachable to said load cells, respectively; and
    a user interface connected to said load cells and said motor, said interface selectively providing signals to said motor to move said turret into contact with a test specimen via one of said indenters to thereby apply a load on the test specimen via said one of said indenters,
    wherein said indenters are fixed with respect to said turret, and wherein said load cells measure the load applied to the test specimen.

2. A hardness tester according to claim 1, further comprising a second frame, movably mounted on said first frame, wherein said turret is rotatably mounted to said second frame, and wherein said motor is connected to said second frame, said motor selectively moving said second frame with respect to said first frame.

3. A hardness tester according to claim 1, further comprising a closed loop control system electrically connected to said motor and said load cells and said user interface, said control loop control system receiving load measurement signals from said load cells and controlling movement of said turret and preventing said motor from applying load in excess of a predetermined selectable load amount input by a user via said user interface.

4. A hardness tester according to claim 3, wherein said closed loop control system is adapted to detect contact between said indenters and the test specimen via said load cells.

5. A hardness tester according to claim 4, further comprising a central processing unit included in said closed loop control system, said central processing unit coordinating signals among said motor, said load cells, and said user interface.

6. A hardness tester according to claim 1, further comprising a linear displacement transducer connected to said turret, sensing the amount of movement of said turret with respect to said first frame.

7. A hardness tester according to claim 2, further comprising a linear displacement transducer connected to said second frame, sensing the amount of movement of said second frame with respect to said first frame.

8. A hardness tester according to claim 7, wherein said linear displacement transducer comprises:
    a scale attached to one of said first and second frames; and
    an optical sensor focused on said scale, attached to the other of said first and second frames, detecting movement of said second frame with respect to said first frame.

9. A hardness tester according to claim 4, further comprising a linear displacement transducer connected to said second frame, sensing the amount of movement of said second frame with respect to said first frame, wherein said linear displacement transducer is connected to said closed loop control system for detecting a position of said turret when said indenter contacts the test specimen.

10. A hardness tester according to claim 1, further comprising:
    at least one optical objective fixedly attachable to said turret; and
    a viewer optically connectable to said at least one optical objective,
    wherein when one of said indenters makes an indentation in a test specimen, said turret is rotatable to position said at least one optical objective over the indentation, and the indentation is viewable by a user via said viewer.

11. A hardness tester according to claim 10, wherein when said turret is rotated to position said at least one optical objective over the test specimen, said optical objective is optically connected to said viewer.

12. A hardness tester according to claim 2, further comprising at least one screw rotatable by said motor and connected to said first and second frames, wherein rotation of said screw by said motor causes said second frame to move with respect to said first frame.

13. A hardness tester according to claim 3, wherein said closed loop control system comprises a proportional integral derivative gain control system with real time stiffness compensation.

14. A hardness tester according to claim 1, wherein said turret is movable in a vertical direction with respect to said first frame.

15. A hardness tester according to claim 1, wherein said second frame is movable in a vertical direction with respect to said first frame.

16. A hardness tester according to claim 1, further comprising a plurality of indenter adapters, each attached to respective undersides of said load cells, each of said indenter adapters including:
a slot into which said indenter is fittable; and
and least one set screw for adjusting a horizontal location of said indenter.

17. A hardness tester according to claim 16, wherein said indenter comprises a pin fittable into said slot, said pin being smaller than said slot.

18. A hardness tester according to claim 17, wherein said indenter adapter further comprises a bore communicating with said slot, said set screw being disposed in said bore, one end of said set screw being abuttable with said pin of said indenter inside said slot.

19. A hardness tester according to claim 18, further comprising a spring-biased member disposed in a second bore formed in said indenter adapter and abuttable with said pin opposite said set screw.

20. A hardness tester according to claim 15, further comprising a plurality of indenter adapters, each attached to respective undersides of said load cells, each of said indenter adapters including:
a slot into which said indenter is fittable; and
and least one set screw for adjusting a horizontal location of said indenter.

21. A hardness tester according to claim 20, wherein said indenter comprises a pin fittable into said slot, said pin being smaller than said slot.

22. A hardness tester according to claim 21, wherein said indenter adapter further comprises a bore communicating with said slot, said set screw being disposed in said bore, one end of said set screw being abuttable with said pin of said indenter inside said slot.

23. A hardness tester according to claim 22, further comprising a spring-biased member disposed in a second bore formed in said indenter adapter and abuttable with said pin opposite said set screw.

* * * * *